United States Patent [19]

Frank et al.

[11] Patent Number: 5,063,925
[45] Date of Patent: Nov. 12, 1991

[54] CONTROLLABLE EXPIRATION VALVE ARRANGEMENT FOR A VENTILATING APPARATUS

[75] Inventors: Helge Frank, Lübeck; Eric Hecker, Stockelsdorf; Reinhard Eifrig, Lübeck; Dieter Weismann, Gross Grönau; Peter Gebhardt, Stockelsdorf, all of Fed. Rep. of Germany

[73] Assignee: Drägerwerk Aktiengesellschaft, Lübeck

[21] Appl. No.: 374,066

[22] Filed: Jun. 30, 1989

[30] Foreign Application Priority Data

Jul. 7, 1988 [DE] Fed. Rep. of Germany ....... 3822950

[51] Int. Cl.$^5$ .......................... A62B 9/02; A61M 16/00
[52] U.S. Cl. ............................ 128/205.24; 128/204.26; 128/204.18
[58] Field of Search ...................... 128/205.24, 205.19, 128/204.26, 204.18

[56] References Cited

U.S. PATENT DOCUMENTS

| 3,385,295 | 5/1968 | Beasley | 128/205.24 |
| 3,486,502 | 12/1969 | Wilson | 128/205.24 |
| 3,905,362 | 9/1975 | Eyrick et al. | 128/205.19 |
| 4,190,045 | 2/1980 | Bartels | 128/205.24 |
| 4,227,523 | 10/1980 | Warnow et al. | 128/205.24 |
| 4,454,893 | 10/1984 | Orchard | 128/205.24 |
| 4,813,409 | 3/1989 | Ismach | 128/205.24 |

FOREIGN PATENT DOCUMENTS

| 2525359 | 12/1975 | Fed. Rep. of Germany . |
| 2573658 | 5/1986 | France | 128/205.24 |

Primary Examiner—Edgar S. Burr
Assistant Examiner—Kimberly L. Asher
Attorney, Agent, or Firm—Walter Ottesen

[57] ABSTRACT

The invention is directed to a controllable expiration valve having a control valve for generating an end expiratory overpressure with the control valve providing the changeable control pressure. The expiration valve is improved so that it is made controllable for compensating dynamic end expiratory overpressure. For this purpose, the membrane chamber of the expiration valve as well as the outflow chamber of the control valve are connected with a device for generating an underpressure.

5 Claims, 3 Drawing Sheets

5,063,925

CONTROLLABLE EXPIRATION VALVE ARRANGEMENT FOR A VENTILATING APPARATUS

FIELD OF THE INVENTION

The invention relates to a controllable expiration valve having a control valve providing a changeable control pressure. A control gas line opens into a control chamber of the expiration valve as well as into a connection of the control valve via a closure element generating a control gas flow pressure.

BACKGROUND OF THE INVENTION

A ventilating apparatus with a control valve for driving a ventilating valve is disclosed in published German Patent Application DT 25 25 359 A1.

In this known ventilating apparatus, the gas necessary for the ventilation flows from the fresh gas metering unit of the ventilating apparatus into a breathing gas hose system which is connected to the patient via a Y-piece. The expiration branch of the hose system is connected to a controllable expiration valve.

The expiration valve is closed during the inspiratory phase so that the ventilating pressure during inhalation can build up in the hose system. However, in the expiration phase, the valve opens and the gas expired by the patient can flow out to the ambient. The control of the expiration valve is achieved with a bistable logic component which serves as a closure element, which, in rhythmic spacing, charges, during the inspiration phase, the control chamber of the expiration valve with a control pressure which closes the valve. For the expiration phase, a switchover to a second lower pressure level occurs by means of which a so-called PEEP-condition is generated in the hose system. PEEP is an acronym which stands for positive end expiratory pressure.

The two pressure levels are adjusted via two switchable branches generating a control pressure via the bistable logic component. Each branch includes a through-flow limiter and a flow throttle. The control gas flowing through the particular through-flow limiter flows off to the atmosphere through the outflow chamber in the closure element and the flow throttle with the developing backpressure functioning as a control pressure on the control chamber of the expiration valve. With the through-flow limiters, the inflowing control gas flow and thereby the control pressure can be varied. The control pressure for the inspiration phase and the expiration phase can be adjusted separately with the through-flow limiters. The bistable logic component in the form of a closure element and the branches generating the control pressure conjointly define the control valve of the expiration valve.

The known expiration valve having the control valve will be referred to in the disclosure which follows as the "expiration valve". These expiration valves have the disadvantage that the least adjustable expiratory pressure is the atmospheric pressure since the control gas can only be released to the atmosphere. The control pressure adjustable at the control valve and thereby the reference pressure present in the control chamber of the expiration valve can be dropped only to the ambient atmosphere as a minimum. However, since the breathing gas encounters a dynamic resistance when flowing through the expiration branch of the breathing gas line, there still always remains the dynamic flow resistance to be overcome in addition to the static reference pressure in the control chamber of the expiratory valve referred to the ambient atmosphere. Thus, this so-called dynamic end expiratory overpressure remains as the breathing gas pressure which must yet be overcome provided that the PEEP at the expiration apparatus was adjusted to zero. In this way, an additional dynamic PEEP pressure is present which has not been calibrated into the entire breathing system even in the presence of a pregiven adjustable PEEP pressure. The PEEP pressure can be different in accordance with the configuration of the expiration apparatus. For this reason, uncontrollable discrepancies can occur between the adjusted PEEP pressure and the actual PEEP pressure.

SUMMARY OF THE INVENTION

It is an object of the invention to make an expiration valve of the kind described above controllable so that the dynamic end expiratory overpressure introduced by the expiration system is considered in the adjustment of the PEEP and compensated for.

According to a feature of the invention, the membrane chamber of the expiration valve as well as the outflow chamber of the control valve are connected with a device generating an underpressure.

The invention provides that the reference pressure in the control chamber of the control valve as well as in the outflow chamber of the control valve has as a minimal value the sub-atmospheric pressure generated by the above device. If this sub-atmospheric reference pressure corresponds to the previously determined dynamic flow resistance, an end expiratory pressure equal to atmospheric pressure can be obtained for operating the expiration valve even in the dynamic case. The unwanted dynamic end expiratory overpressure is thereby compensated.

The generated sub-atmospheric pressure is effective in the control chamber as well as in the membrane chamber of the expiration valve when the closure force on the closure element of the control valve is completely withdrawn (unthrottled control gas flow). With a subsequent adjustment of the closure force at the closure element of the control valve, the sub-atmospheric pressure is raised until it corresponds in magnitude to the dynamic expiration pressure and thereby compensates the latter. Typically, an underpressure of up to 15 mbar is generated by the device with a pumping capacity of more than approximately 30 L/min. The control gas flows with a typical flow of approximately 1 L/min. The suction characteristic of the device generating the underpressure is not affected by this relationship of pumping capacity and flow velocity.

An advantageous device for generating the underpressure includes a suction pump either in the form of a volume pump or also in the form of a flow ejector generating an underpressure.

It is advantageous to configure the control valve as a membrane valve whose pressure control chamber as a portion of the outflow chamber is likewise connected to the device generating the underpressure. It can be adequate to configure the outflow chamber as a chamber in which only the closure element in the form of an element generating the reference pressure is accommodated.

It is advantageous to select a plunger-coil or solenoid arrangement in order to apply a reliable and easily controllable closure force to the closure element of the control valve during the inhaling and exhaling phases.

This solenoid arrangement can be driven via a control unit in dependence upon the expiration phase with respect to its closure force. During the inspiration, the entire closure force, for example, operates on the closure element. The reference pressure acting in the control chamber of the expiration valve closes the expiration valve. The solenoid can act via a rod on the closure element in the control chamber of the control valve.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
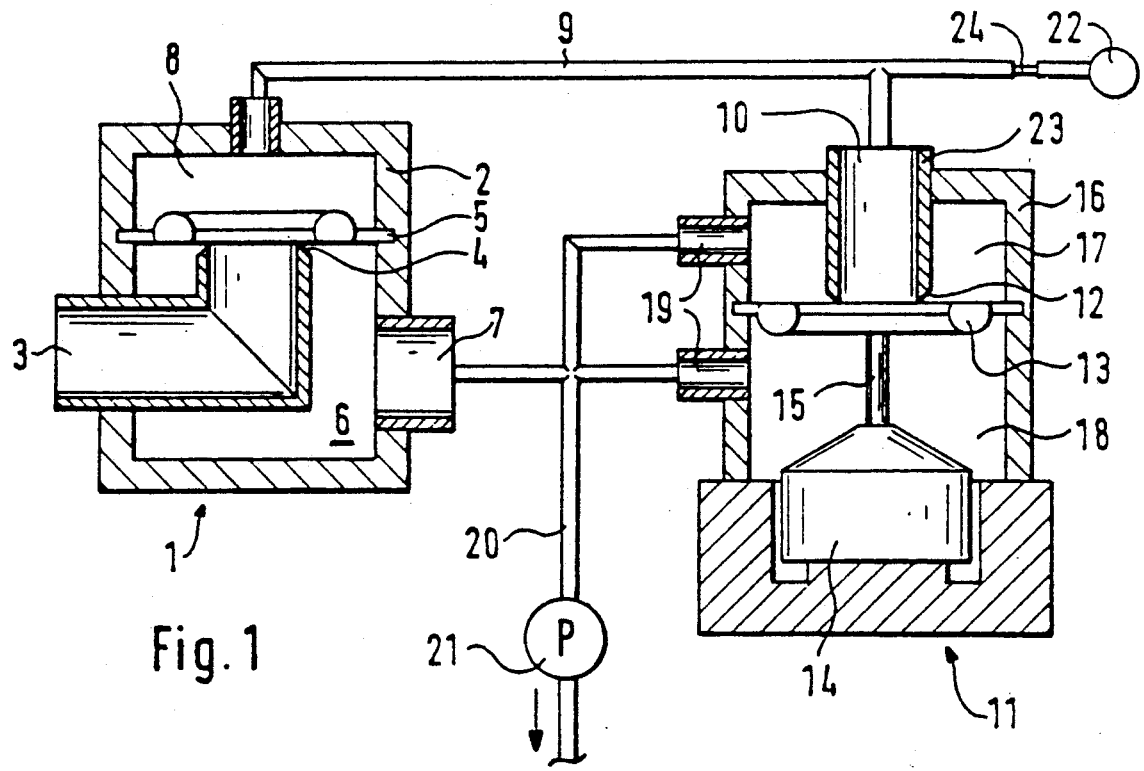
FIG. 1 is a schematic showing the interconnection between the expiration valve and the control valve equipped with a plunger-coil arrangement.

FIG. 1 discloses an expiration valve 1 having a valve housing 2 which includes an inlet 3 for the breathing gas from the expiratory branch of a breathing gas line (not shown). The inlet 3 opens into a crater valve seat 4 which is covered by a membrane 5. The membrane chamber 6 of the expiration valve 1 includes an outlet 7. A control gas line 9 opens into the control chamber 8 which is simultaneously connected to a control inlet 10 of a control valve 11.

Figure 1A:
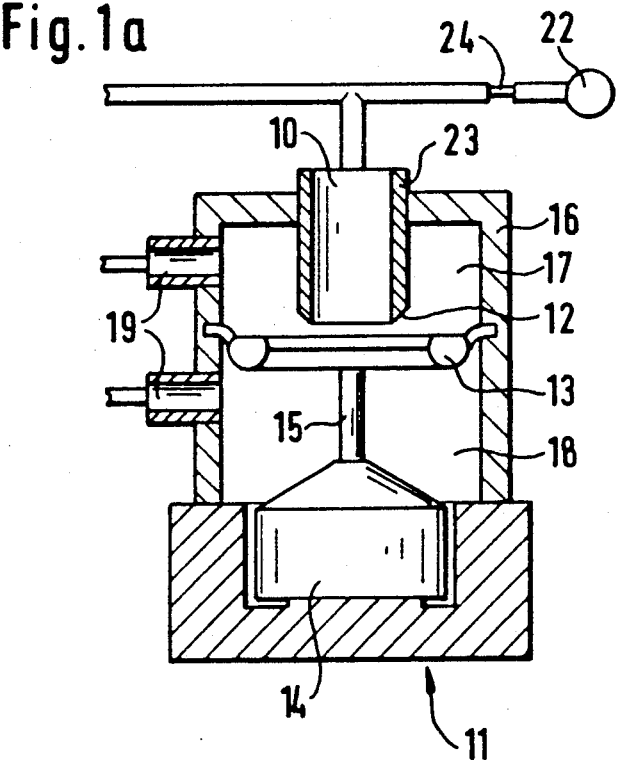
FIG. 1a is a view of the control valve of the expiration valve control arrangement of FIG. 1 showing the control membrane of the control valve in its open position.

The control inlet 10 terminates in a valve seat 12 for a control membrane 13 which for its closure force is pretensioned in the closure direction by means of a plunger-coil arrangement 14 and a push rod 15 acting on the control membrane 13. The control membrane 13 is shown in its closed position in FIG. 1 and in its open position in FIG. 1a. The housing 16 of the control valve 11 is partitioned by the control membrane 13 into an outflow chamber 17 and a pressure-control chamber 18. Both chambers (17, 18) are provided with outlets 19 which, together with outlet 7 of the expiration valve, are connected to a suction line 20 which is connected to a suction pump 21 for generating the underpressure. The control gas is pumped from a control gas source 22 via a throttle 24 into the control gas line 9. The throttle 24 limits the control gas flow such that the same pressure is present in the control chamber 8 as in the control inlet 10.

During operation, the full closure force acts on the control membrane 13 during inspiration. The control chamber 8 is charged with the maximum control pressure via the control gas line 9. The membrane 5 is pressed against the crater valve seat 4 and the expiration valve 1 is closed. With the beginning of the expiration, the closure force on the control membrane 13 is reduced so far that the expiration valve 1 is opened and the previously determined end expiratory overpressure self-adjusts.

The end expiratory pressure can be so adjusted via the closure force that the dynamic end expiratory pressure acting in the breathing gas line is considered and is fully compensated.

Figure 2:
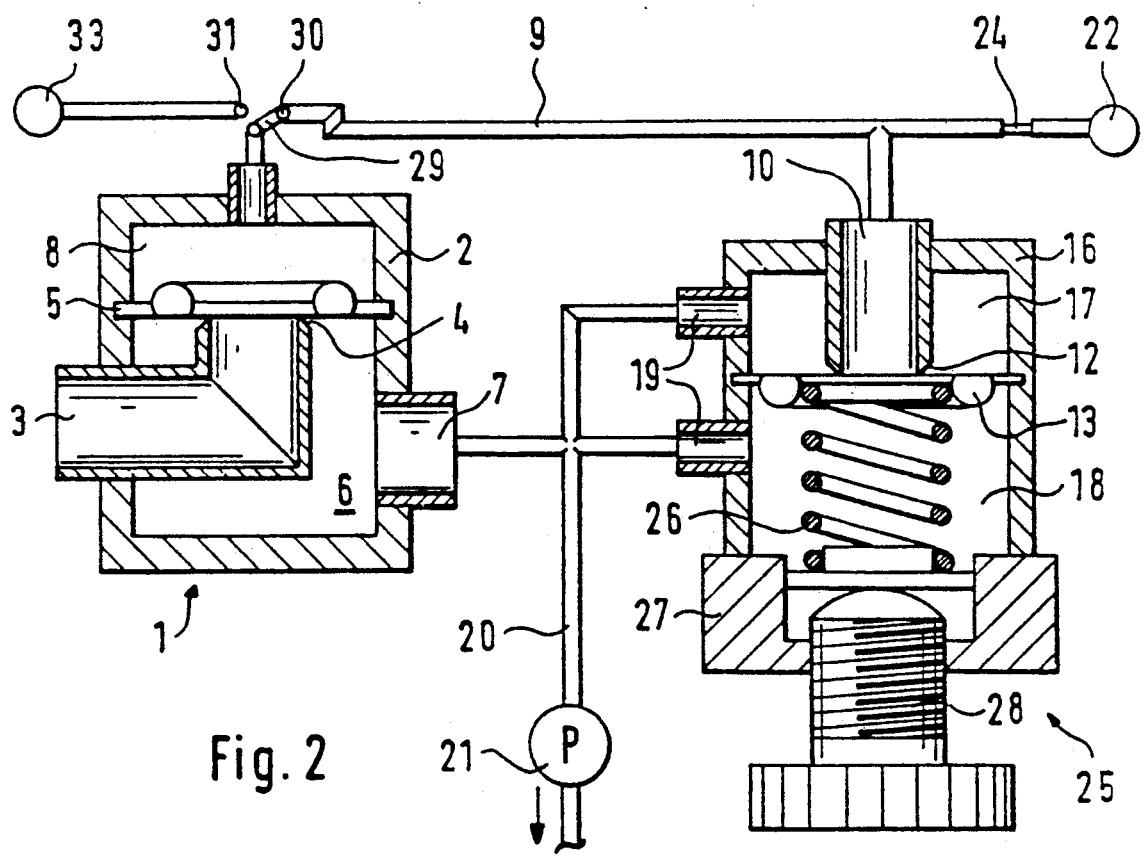
FIG. 2 is a schematic of another embodiment of the controllable expiration valve wherein the control valve includes a spring-biased control membrane.
Figure 2B:
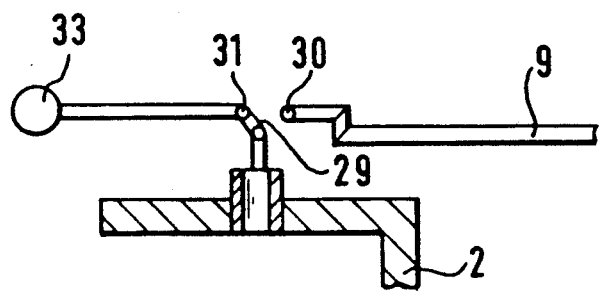
FIG. 2a is a view of the control valve of the expiration valve control arrangement of FIG. 2 showing the control membrane of the control valve in its open position; and, FIG. 2b shows the throwover switch of the expiration valve control arrangement of FIG. 2 shown connected to the first connecting port.
Figure 2A:
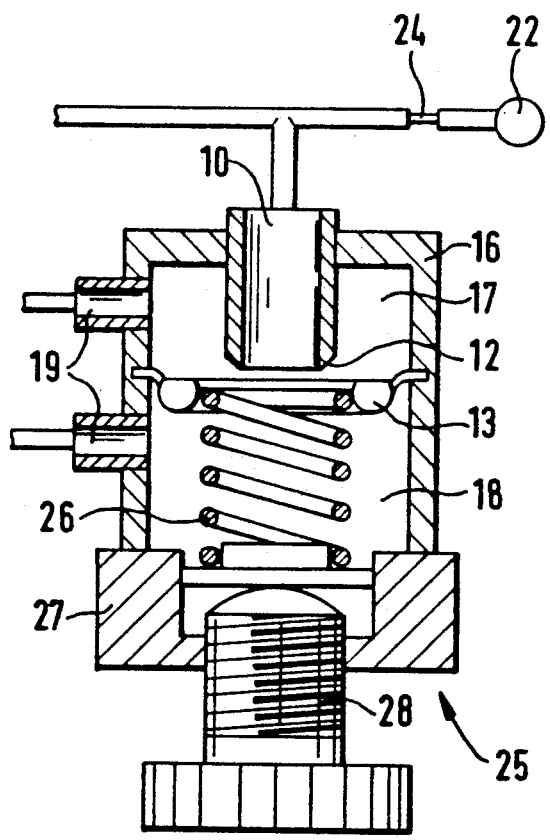

FIG. 2 shows an alternate embodiment of a control valve 25 equipped with a spring-loaded control membrane 13. The reference numerals used in FIG. 2 are the same as those in FIG. 1 insofar as the same elements are utilized and the description for FIG. 1 applies analogously. The control membrane 13 is shown in its closed position in FIG. 2 and in its open position in FIG. 2a.

The control membrane 13 is pretensioned by the spring 26 with the pretensioned force being adjustable by the knurled screw 28. The knurled screw is guided in the housing 27. The control gas flows from two sources 22 and 33. During inspiration, the throwover switch 29 is connected via the second connector 31 (See FIG. 2b) to the control gas source 33 which charges the control chamber 8 with pressure. The expiration valve 1 is closed.

In the expiratory phase, the control chamber 8 is connected with the control gas source 22 via the throwover switch 29 and the first connector 30. The reference pressure in the control chamber 8 is adjusted by the closure force of the spring 26. The closure force of the spring 26 is changeable with the knurled screw 28.

It is understood that the foregoing description is that of the preferred embodiments of the invention and that various changes and modifications may be made thereto without departing from the spirit and scope of the invention as defined in the appended claims.

What is claimed is:

1. A controllable expiration valve arrangement for a ventilating apparatus having an expiration branch line said expiration branch line producing a dynamic flow resistance as the exhaled breathing gas flows therethrough said dynamic flow resistance producing a dynamic end expiratory pressure in the expiration branch line, the arrangement comprising:

an expiration valve having an expiration valve housing and membrane valve means for partitioning said housing into a control chamber and a membrane chamber;

an inlet for admitting breathing gas into said membrane chamber from the branch line of the ventilating apparatus;

said membrane valve means being switchable between a closed position during inspiration so as to close said inlet and an open position during expiration so as to open said inlet to communicate with said membrane chamber;

means for compensating for said dynamic positive end expiratory pressure comprising;

a control valve for maintaining a desired end expiratory pressure during expiration by providing a changeable pressure to said control chamber for actuating said membrane valve means to switch between said closed end said open position, said control valve having a control valve housing and a control membrane for partitioning said control valve housing into first and second chambers;

underpressure means for generating an underpressure in said first and second chambers of said control valve and in said membrane chamber of said expiration valve corresponding to said dynamic positive end expiratory pressure.

control gas line means communicating with said control chamber of said expiration valve and said control membrane for supplying a control gas under pressure thereto;

said control valve including valve seat means communicating with said control gas line means;

said control membrane being mounted in said control valve housing for coacting with said valve seat means for closing said valve seat means; and, said control valve further including force applying means for applying a first force to said control membrane during said inspiration and for applying a second force to said control membrane during expiration which is reduced to be less than said first force for reducing the pressure of said control gas applied to said membrane valve means of said expiration valve to cause said membrane valve means to open, and for compensating for the dynamic end expiratory pressure acting in the branch line in combination with said underpressure means.

2. The controllable expiration valve arrangement of claim 1, said underpressure means comprising a suction pump connected to said first and second chambers and said membrane chamber.

3. A controllable expiration valve arrangement for a ventilating apparatus, the arrangement comprising:

an expiration valve having an expiration valve housing and membrane valve means for partitioning said housing into a control chamber and a membrane chamber;

said membrane valve means being switchable between a closed position during inspiration and an open position during expiration;

a control valve for providing a changeable pressure to said control chamber for actuating said membrane valve means to switch between said positions, said control valve having a control valve housing and closure means for partitioning said control valve housing into first and second chambers;

control gas line means communicating with said control chamber and said closure means for supplying a control gas under pressure thereto;

said closure means including valve seat means communicating with said control gas line means; a closure member for closing said valve seat means; and, force applying means for applying a first force to said closure member during said inspiration and for applying a second force to said closure member during expiration which is less than said first force thereby changing the pressure of said control gas applied to said membrane valve means;

underpressure means for generating an underpressure in at least one of said first and second chambers of said control valve and in said membrane chamber of said expiration valve;

said closure member being a control membrane partitioning said control chamber housing into said first and second chambers;

said force applying means being an actuator for actuating said control membrane; and, said underpressure means being connected to both of said first and second chambers for generating an underpressure therein.

4. The controllable expiration valve arrangement of claim 3, said actuator comprising a plunger-coil arrangement having a moveable push rod connected to said control membrane and biasing the latter so as to close the same against said valve seat means.

5. A controllable expiration valve arrangement for a ventilating apparatus, the arrangement comprising:

an expiration valve having an expiration valve housing and membrane valve means for partitioning said housing into a control chamber and a membrane chamber;

said membrane valve means being switchable between a closed position during inspiration and an open position during expiration;

a control valve having a control valve housing and closure means for partitioning said control valve housing into first and second chambers;

first control gas supply means for supplying a first control gas at a first control pressure;

second control gas supply means for supplying a second control gas at a second control pressure;

switchover means movable into a first switching position for connecting said first control gas supply means to said control chamber of said expiration valve during inspiration to move said membrane valve means into said closed position and then movable out of said first switching position and into a second switching position for connecting said second control gas supply means to said control chamber of said expiration valve during expiration to switch said membrane valve means into said open position while at the same time also connecting said second control gas supply means to said closure means;

said closure means including valve seat means disposed in said first chamber; a valve closure member for coacting with said valve seat means; and, adjustable force means for applying an adjusted force to said valve closure member for adjusting the magnitude of said second control pressure in said control chamber during said expiration; and, underpressure means for generating an underpressure in at least one of said first and second chambers of said control valve and in said membrane chamber of said expiration valve.

* * * * *

UNITED STATES PATENT AND TRADEMARK OFFICE
CERTIFICATE OF CORRECTION

PATENT NO. : 5,063,925

DATED : November 12, 1991

INVENTOR(S) : Helge Frank, Eric Hecker, Reinhard Eifrig, Dieter Weismann and Peter Gebhardt It is certified that error appears in the above-identified patent and that said Letters Patent is hereby corrected as shown below:

In column 1, line 16: delete "ventilating" and substitute -- expiration -- therefor.

In column 4, line 39: between "through" and "said" insert -- , --.

In column 4, line 60: delete "end" and substitute -- and -- therefor.

In column 4, line 68: after "pressure" insert -- ; --.

Signed and Sealed this

Sixteenth Day of March, 1993

Attest:

STEPHEN G. KUNIN

Attesting Officer   Acting Commissioner of Patents and Trademarks